US010610377B2

(12) United States Patent
Baynham

(10) Patent No.: US 10,610,377 B2
(45) Date of Patent: Apr. 7, 2020

(54) SPINAL IMPLANT DEVICE

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 0 days.

(21) Appl. No.: 16/047,152

(22) Filed: Jul. 27, 2018

(65) Prior Publication Data

US 2019/0021871 A1 Jan. 24, 2019

Related U.S. Application Data

(63) Continuation-in-part of application No. 15/874,351, filed on Jan. 18, 2018, now Pat. No. 10,322,011, which is a continuation-in-part of application No. 15/664,891, filed on Jul. 31, 2017, now Pat. No. 10,034,767, which is a continuation-in-part of application No. 14/642,992, filed on Mar. 10, 2015, now Pat. No. 9,717,605, which is a continuation-in-part of application No. 14/294,889, filed on Jun. 3, 2014, now Pat. No. 9,445,920.

(51) Int. Cl.
*A61F 2/44* (2006.01)
*A61F 2/30* (2006.01)

(52) U.S. Cl.
CPC .......... *A61F 2/447* (2013.01); *A61F 2/30771* (2013.01); *A61F 2/4455* (2013.01); *A61F 2002/3039* (2013.01); *A61F 2002/3093* (2013.01); *A61F 2002/30153* (2013.01); *A61F 2002/30263* (2013.01); *A61F 2002/30281* (2013.01); *A61F 2002/30405* (2013.01); *A61F 2002/30482* (2013.01); *A61F 2002/30507* (2013.01); *A61F 2002/30538* (2013.01); *A61F 2002/30556* (2013.01); *A61F 2002/30578* (2013.01); *A61F 2002/30593* (2013.01); *A61F 2002/30827* (2013.01); *A61F 2002/30904* (2013.01); *A61F 2002/30934* (2013.01); *A61F 2002/4475* (2013.01)

(58) Field of Classification Search
CPC .. A61F 2002/30535; A61F 2002/30576; A61F 2002/30578; A61F 2002/30579; A61F 2/44; A61F 2/447; A61F 2/4455; A61F 2/442; A61F 2/4425; A61F 2002/443; A61F 2002/4475
USPC ..................... 606/246–249; 623/17.11–17.16
See application file for complete search history.

(56) References Cited

U.S. PATENT DOCUMENTS

| 8,556,979 | B2 | 10/2013 | Glerum et al. |
| 8,709,086 | B2 * | 4/2014 | Glerum .................. A61F 2/447 623/17.16 |
| 2006/0122701 | A1 | 6/2006 | Kiester |
| 2009/0292361 | A1 | 11/2009 | Lopez |
| 2010/0292796 | A1 | 11/2010 | Greenhalgh et al. |
| 2011/0093074 | A1 | 4/2011 | Glerum et al. |

(Continued)

*Primary Examiner* — Julianna N Harvey
*Assistant Examiner* — Christina Negrelli-Rodriguez
(74) *Attorney, Agent, or Firm* — McHale & Slavin, P.A.

(57) ABSTRACT

A spinal fusion device that is expandable along a side edge. The device features a top and bottom surface for engaging adjacent vertebrae, a hollow center for stacking of bone or bone growth material, and a slidable mechanism with grooves for expanding or contracting the device along a side edge.

9 Claims, 15 Drawing Sheets

(56) References Cited

U.S. PATENT DOCUMENTS

2012/0226356 A1  9/2012  Hirschl
2013/0006361 A1  1/2013  Glerum et al.

\* cited by examiner

SPINAL IMPLANT DEVICE

PRIORITY CLAIM

In accordance with 37 C.F.R. 1.76, a claim of priority is included in an Application Data Sheet filed concurrently herewith. Accordingly, the present invention claims priority as a continuation-in-part of U.S. patent application Ser. No. 15/874,351, entitled "SPINAL IMPLANT DEVICE WITH BONE SCREWS", filed Jan. 18, 2018, which is a continuation-in-part of U.S. patent application Ser. No. 15/664,891, entitled "SPINAL IMPLANT DEVICE", filed Jul. 31, 2017, which is a continuation-in-part of U.S. patent application Ser. No. 14/642,992, entitled "SPINAL IMPLANT DEVICE", filed Mar. 10, 2015, now U.S. Pat. No. 9,717,605, issued Aug. 1, 2018, which is a continuation-in-part of U.S. patent application Ser. No. 14/294,889, entitled "SPINAL IMPLANT DEVICE", filed Jun. 3, 2014, now U.S. Pat. No. 9,445,920, issued on Sep. 20, 2016. The contents of the above referenced applications are incorporated herein by reference.

FIELD OF THE INVENTION

Embodiments of the invention relate to the field of orthopedic surgery and, more particularly, to implants to be placed between vertebrae in the spine.

BACKGROUND

Spinal stabilization is one approach to alleviating chronic back pain caused by disabled disk material or excessive movement of individual vertebrae. Conventional stabilization techniques include fusing two or more vertebrae together to circumvent or immobilize the area of excessive movement. Normally, the vertebral disk material which separates the vertebrae is removed and bone graft material is inserted in the space for interbody fusion. In addition to, or in place of, the bone graft material, a spinal implant may be inserted in the intervertebral space.

The conventional surgical approach for stabilization has been posteriorly for ease of access to the spine and to avoid interfering with internal organs and tissues. Usually, the implant site is prepared to maintain natural lordosis and to accept a certain sized implant within certain pressure limits. This requires considerable time and skill by the surgeon. U.S. Pat. No. 8,556,979, issued Oct. 15, 2013, describes an expandable fusion device capable of being installed inside an intervertebral disc space to maintain normal disc spacing and restore spinal stability. The fusion device includes a body portion, a first end plate, and a second end plate; both of these end plates can be moved in a direction away from the body portion or towards the body portion into an unexpanded configuration.

SUMMARY OF THE INVENTION

Embodiments of the invention are directed to an expandable spinal fusion device comprising upper and lower sections with depending sidewalls forming a cube-like or rectangular structure with a hollow center. The upper and lower sections comprise a top and a bottom surface, respectively, for engaging adjacent vertebrae, a slidable mechanism for expanding or compacting the device, and a hollow center allowing for packing with bone graft or similar bone growth inducing material. The slidable mechanism comprises slots or grooves on each of the sidewalls depending from the top and bottom surfaces, and a distractor. The distractor comprises a rod, a body and an actuator for enabling distraction. The rod can be telescopic or a jack screw type rod. The distractor comprises a body with protruding members, rollers or pins, for engaging the grooves which are positioned in the exact location directly opposite from each other. When the distractor is actuated, the body slides upwards, downwards or sideways depending on the groove geometry.

The device is inserted between the adjacent vertebrae and expanded or increased in height to engage the opposing surfaces of the adjacent vertebra. The adjacent vertebrae are forced apart as the height of the implant increases. The spinal fusion device may be used unilaterally or bilaterally.

Accordingly, it is an objective of the instant invention to teach a posterior surgical approach for placement of an adjustable spinal implant for interbody fusion, allowing the implant to be inserted through a small incision and increased in size in situ.

It is another objective of the instant invention to teach a spinal implant which allows the surgeon to provide for lordosis intraoperatively and to distract through the implant.

It is yet another objective of the instant invention to teach an implant facilitating interbody fusion through bone graft or an ingrowth type implant.

Although embodiments are directed to posterior surgical approaches and to provide for lordosis intraoperatively, it is to be understood that the invention may be employed in cervical and thoracic spinal procedures, as well as from any direction, that is, anterior, posterior and lateral.

Other objectives and advantages of this invention will become apparent from the following description taken in conjunction with the accompanying drawings wherein are set forth, by way of illustration and example, certain embodiments of this invention. The drawings constitute a part of this specification, include exemplary embodiments of the present invention, and illustrate various objects and features thereof.

DETAILED DESCRIPTION

Figure 1:
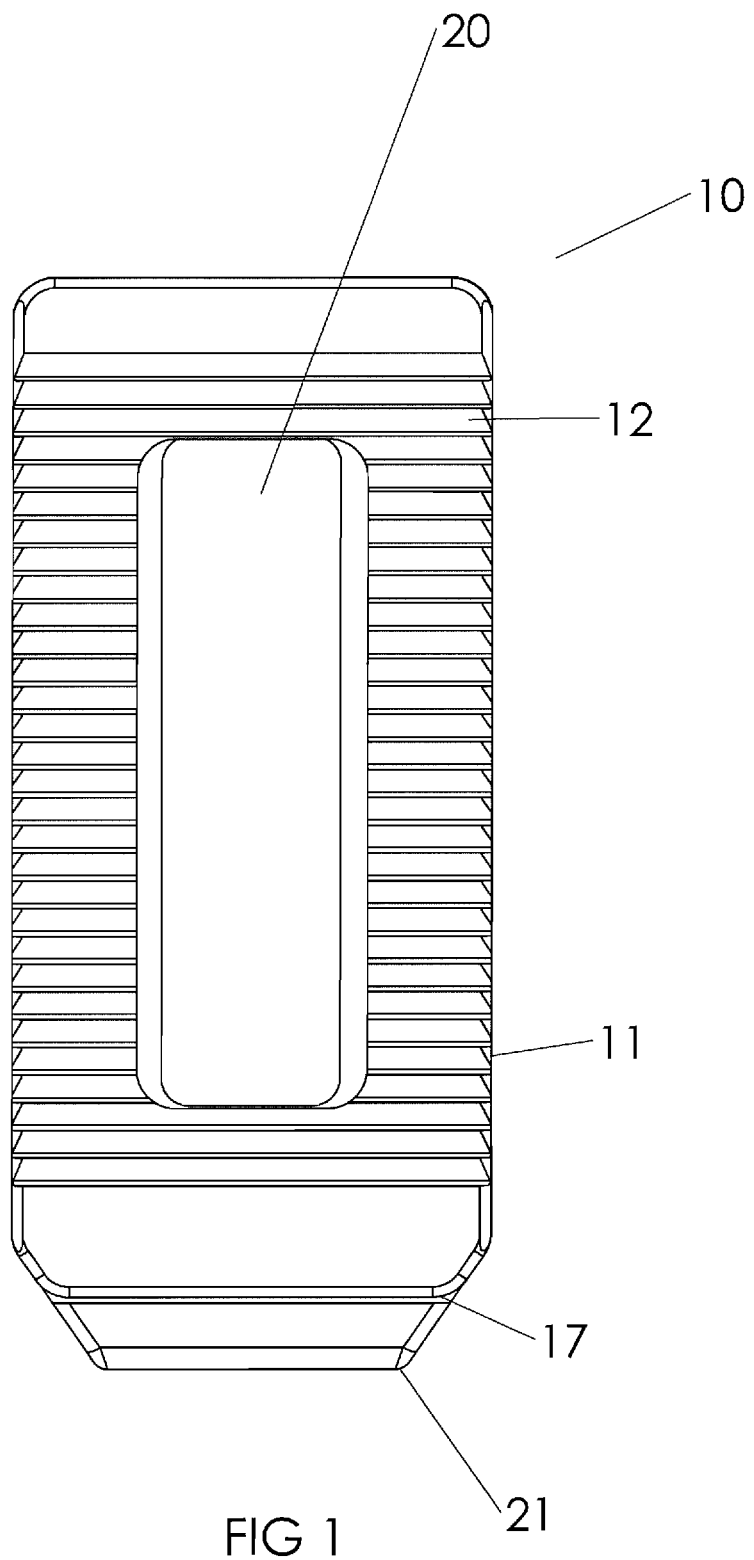
FIG. 1 is a top view of the implant in a closed position.

The following description of the preferred embodiments is merely exemplary in nature and is in no way intended to limit the invention, its application or uses. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention may be practiced without the theoretical aspects presented. Moreover, the theoretical aspects are presented with the understanding that Applicants do not seek to be bound by the theory presented.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

A spinal fusion is typically employed to eliminate pain caused by the motion of degenerated disk material. Upon successful fusion, a fusion device becomes permanently fixed within the intervertebral disc space.

Referring now to the Figures, in an exemplary embodiment, the spinal implant device 10, has an upper section 11, a lower section 13, a body portion 18 and a distractor 55. The device may be made of conventional materials used for surgical implants, such as stainless steel and its many different alloys, titanium, titanium alloys, metallic alloys, polymeric materials, plastics, plastic composites, ceramics, and any other metal or material with the requisite strength and biologically inert properties.

The upper section 11 is further defined by a top surface 12, a first sidewall 23, and a second sidewall 24. The first sidewall 23 has three angle sloped grooves 70 to engage with the protruding members 52 on one side of the distractor 55, and the second sidewall 24 has three straight sloped grooves 73 for engaging protruding members 53 on a second side of said distractor 55.

The top surface 12 has an aperture 20 allowing for a channel to the interior of the distractor. There is a sloping or angled leading edge 15 of the upper section 11 which abuts the housing end edge 17 of the body portion 18 when the upper section 11 is in a non-expanded position. A basic geometry of the grooves is depicted in the Figures; however, it will be understood by one skilled in the art that the geometry of the grooves can be altered to change the distances between the upper and lower sidewall edges of the sections.

The lower section 13 is constructed to cooperate with the upper section 11, having a bottom surface 14, a first sidewall 40, and a second sidewall 41. The first sidewall 40 has three angle sloped grooves 71, having a mirror image configuration to the three angle sloped grooves 70 of the upper section 11, engaging the protruding members 52 on the distractor 55. The second sidewall 41 has three straight sloped grooves 75 for engaging the protruding members 53 of the distractor 55. The bottom surface 14 has an aperture 77 allowing access to an interior area of the distractor 55. There is an angled leading edge 79 which abuts the housing end edge 17 of the body portion 18 in a non-expanded position.

A body portion 18 has apertures 28, 29 on opposing sidewalls 26, 27 which act as channels for the protruding members 52, 53 of the distractor 55, allowing the distractor 55 to move along a longitudinal axis of the body portion 18. The opening 60 of the second end 19 of the body portion 18 is enlarged in the preferred embodiment, allowing passage of an actuation member 51 and spacer 50 therethrough. The actuation member 51 cooperates with the support aperture 79 on the housing end 21 of the body portion 18, wherein actuation moves the distractor 55 along the longitudinal axis of the body portion 18 towards the housing end edge 17. The distractor 55 has an opening 89 to create a passage for adjustment of the actuation member 51.

The upper section 11 of the device 10 comprises a top surface 12 having directional teeth 19 for engaging the end plate of a vertebra. Similarly, the lower section 13 comprises a bottom surface 14 having directional teeth 29 for engaging the end plate of adjacent vertebra. The top surface 12 and bottom surface 14 are planar to provide large contact areas with each vertebra. In other embodiments, the top and bottom surfaces may have sloped edges.

The spinal implant device 10 is hollow, allowing for insertion of bone graft, bone graft material, scaffolds or any tissue or cellular material. In one embodiment, bone graft or similar bone growth inducing material can be introduced around and within the fusion device to further promote and facilitate bone fusion. The fusion device is hollow in the center, further providing a space for packing with bone graft or similar bone growth inducing material. Such bone graft or bone growth inducing material can be packed, prior to, subsequent to, or during implantation of the fusion device.

Figure 2:
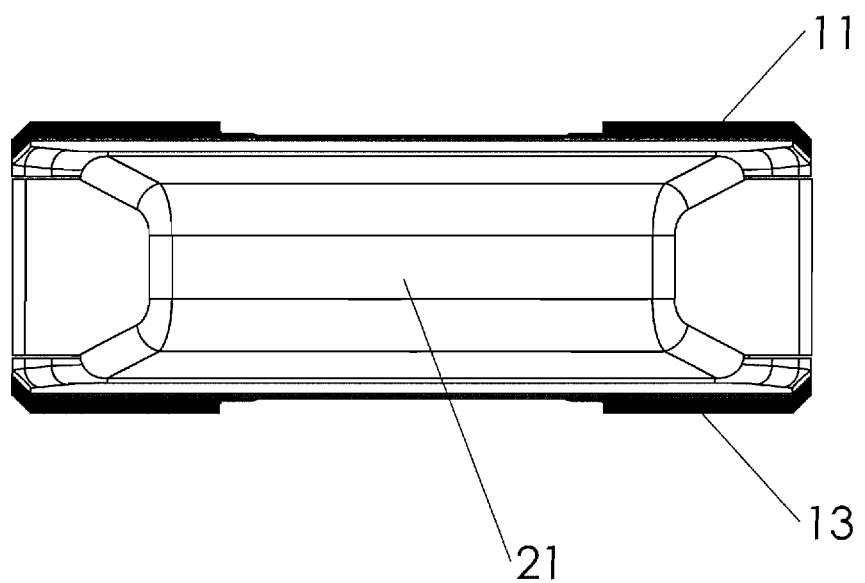
FIG. 2 is a front view thereof.
Figure 3:
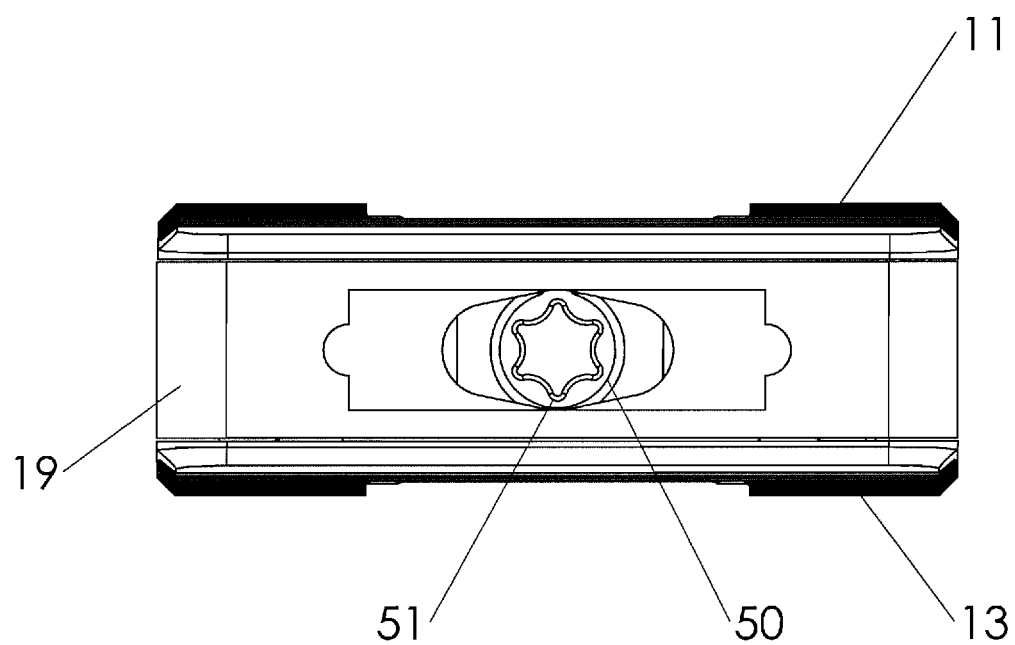
FIG. 3 is a rear view thereof.
Figure 4:
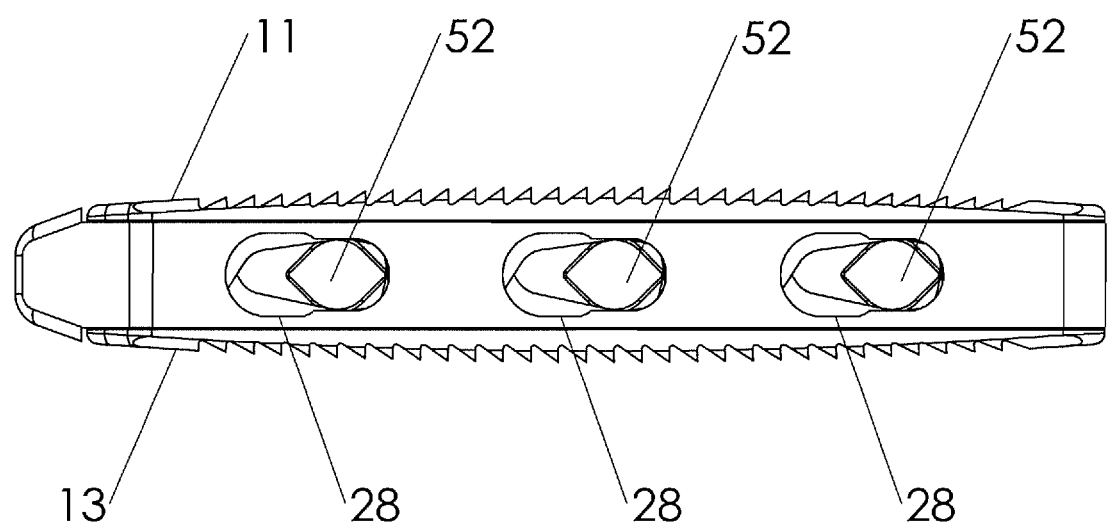
FIG. 4 is a left side view thereof.
Figure 5:
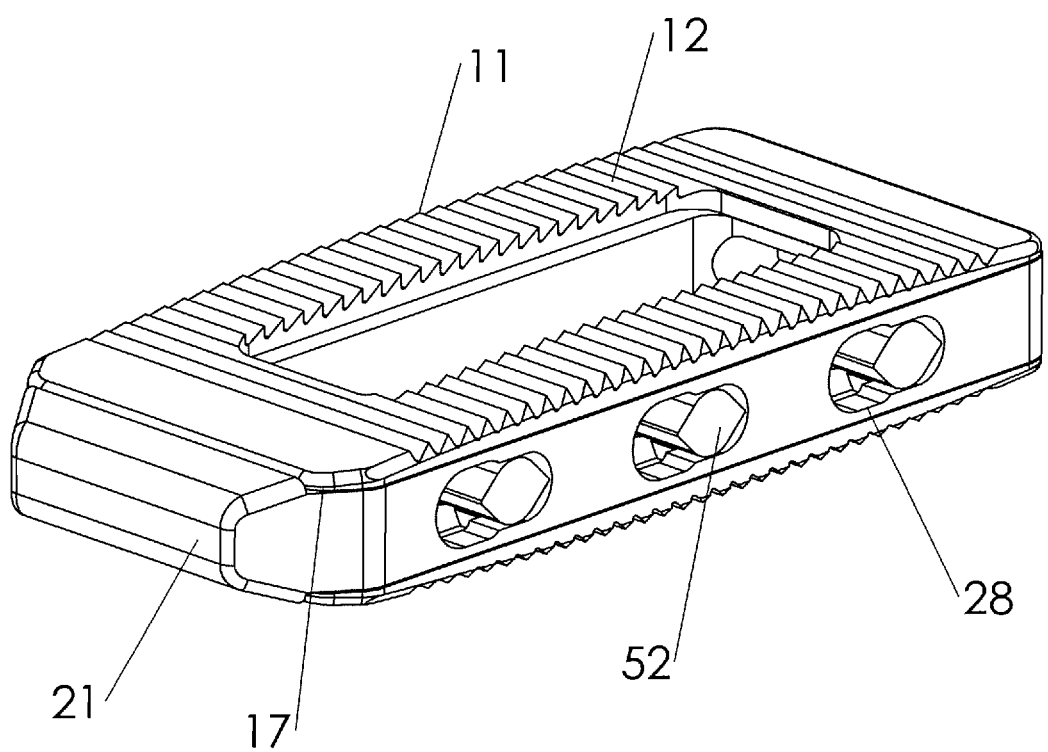
FIG. 5 is a front left perspective view thereof.
Figure 6:
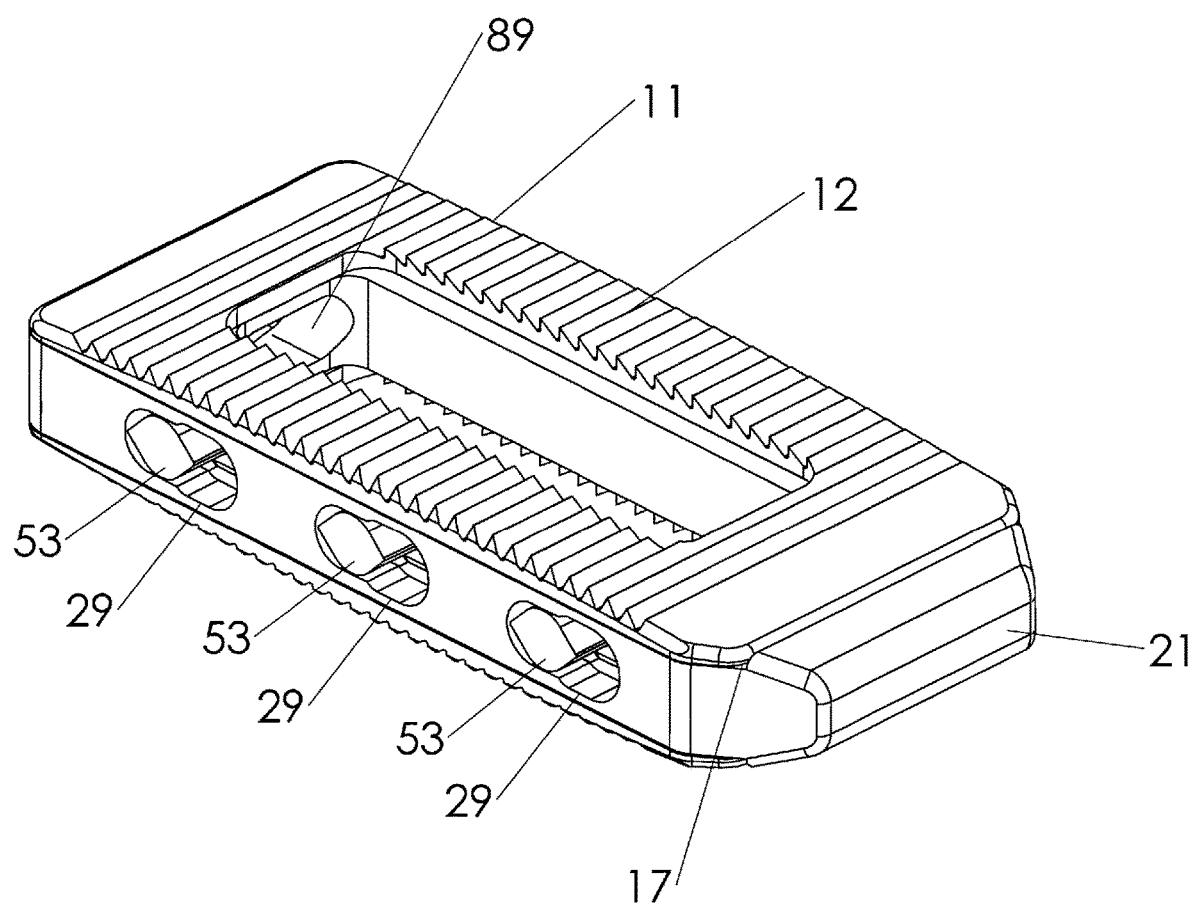
FIG. 6 is a front right perspective view thereof.
Figure 7:
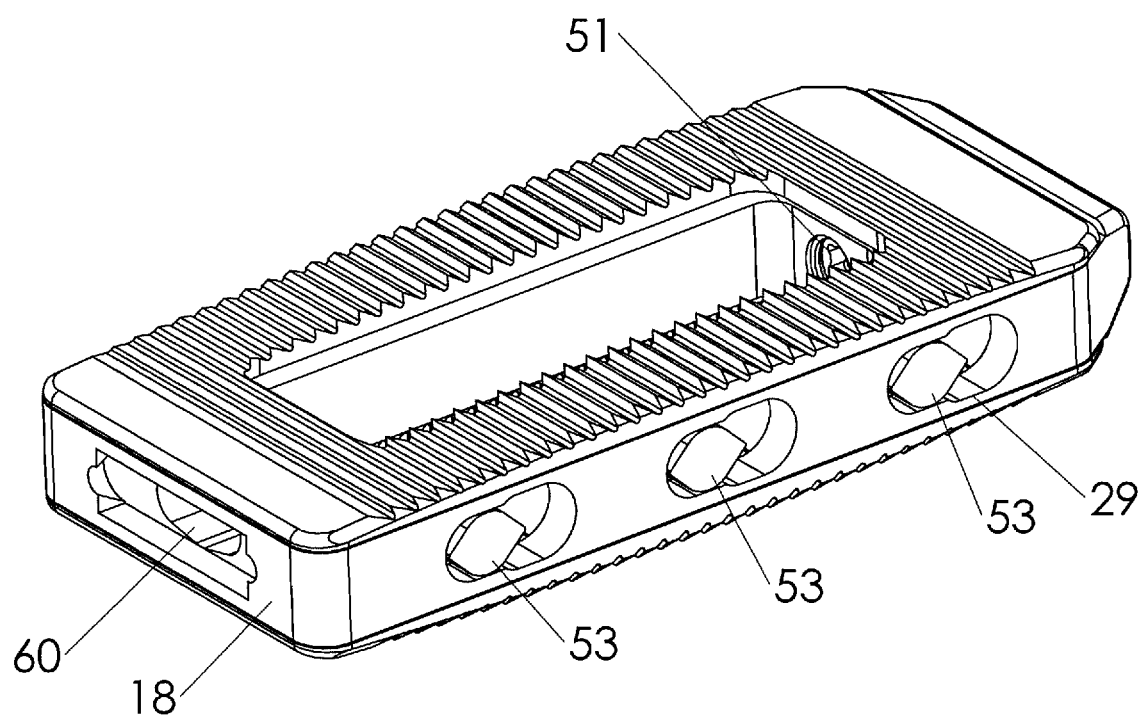
FIG. 7 is a rear right perspective view thereof.
Figure 8:
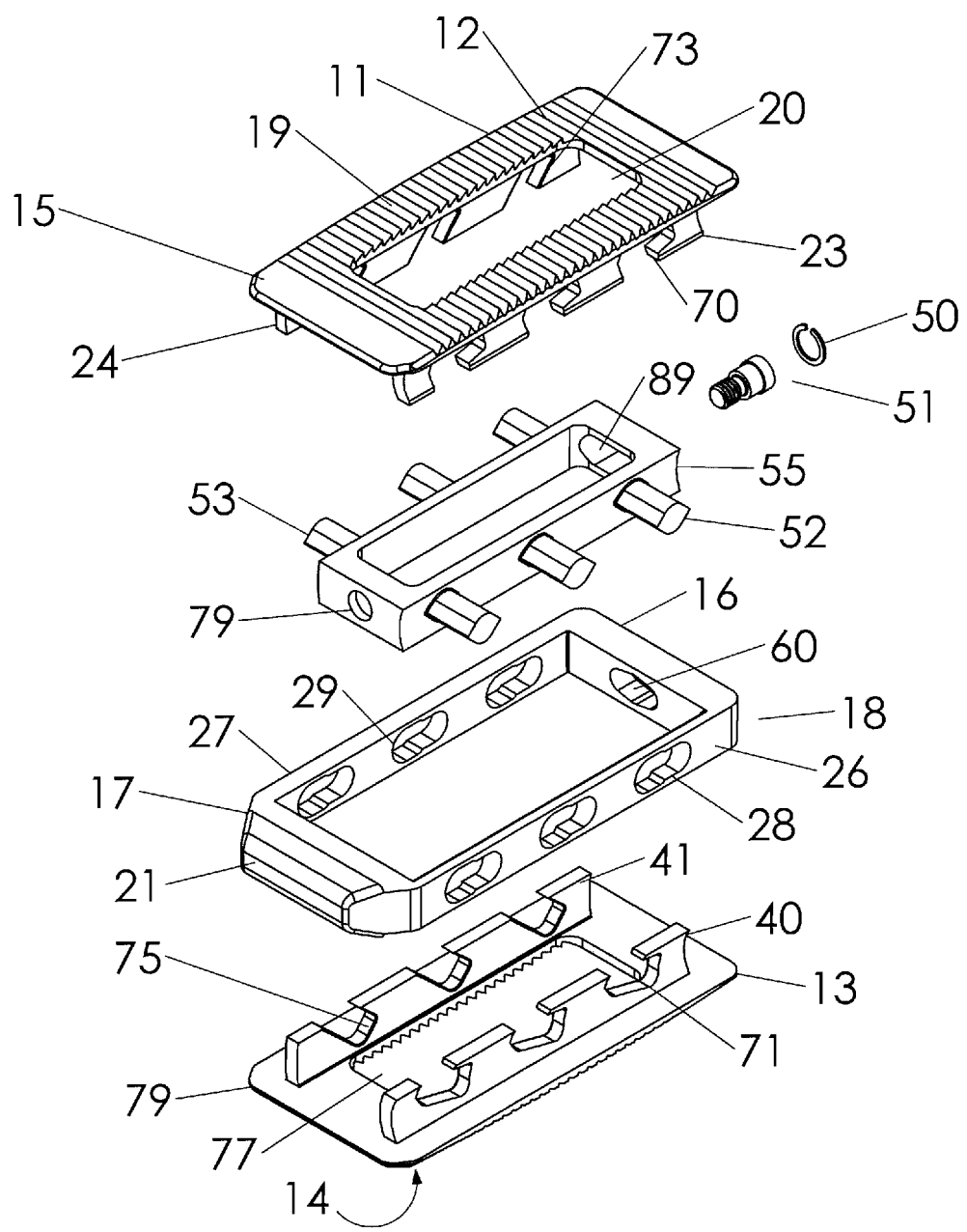
FIG. 8 is an exploded view of the implant.
Figure 9:
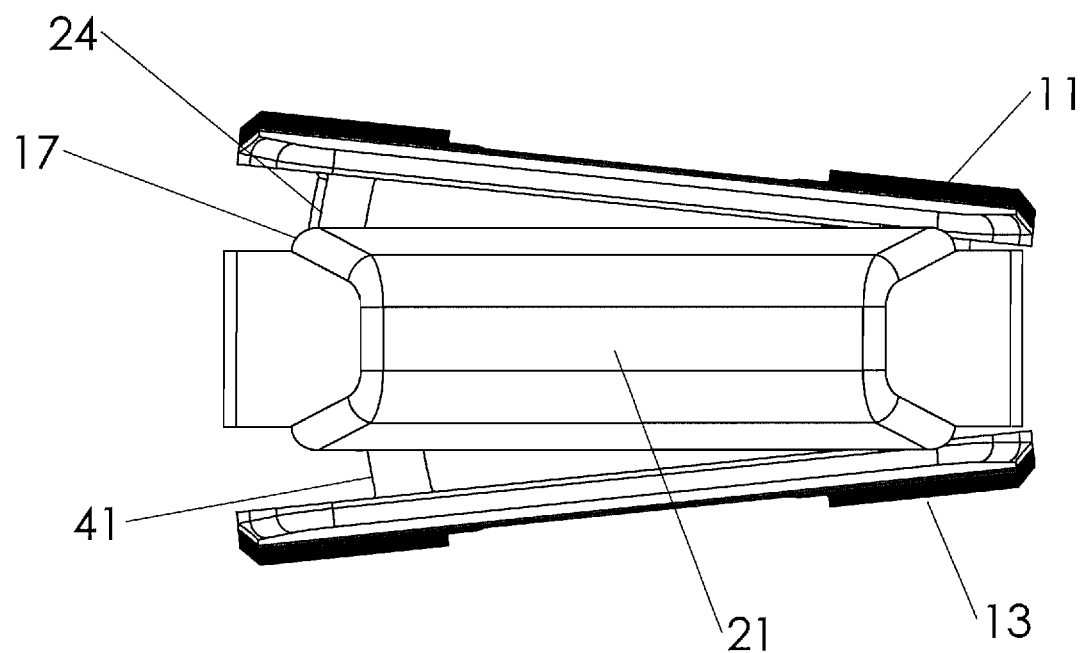
FIG. 9 is a front view of the implant in an expanded position.
Figure 10:
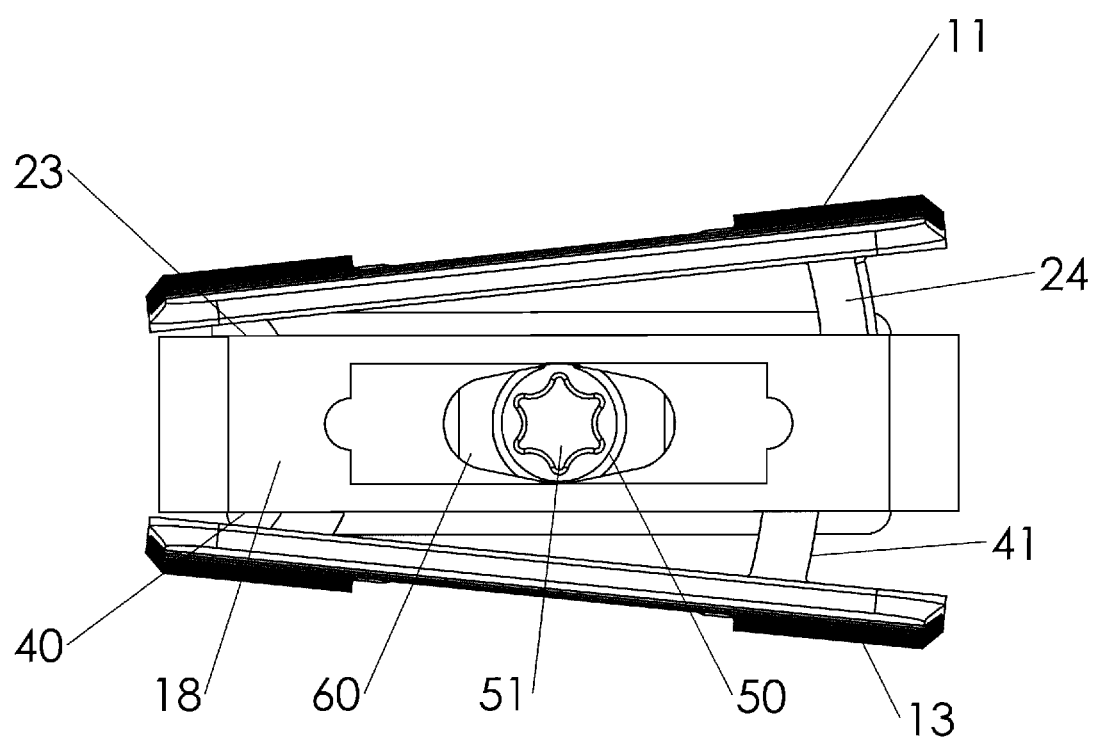
FIG. 10 is a rear view thereof in an expanded position.
Figure 11:
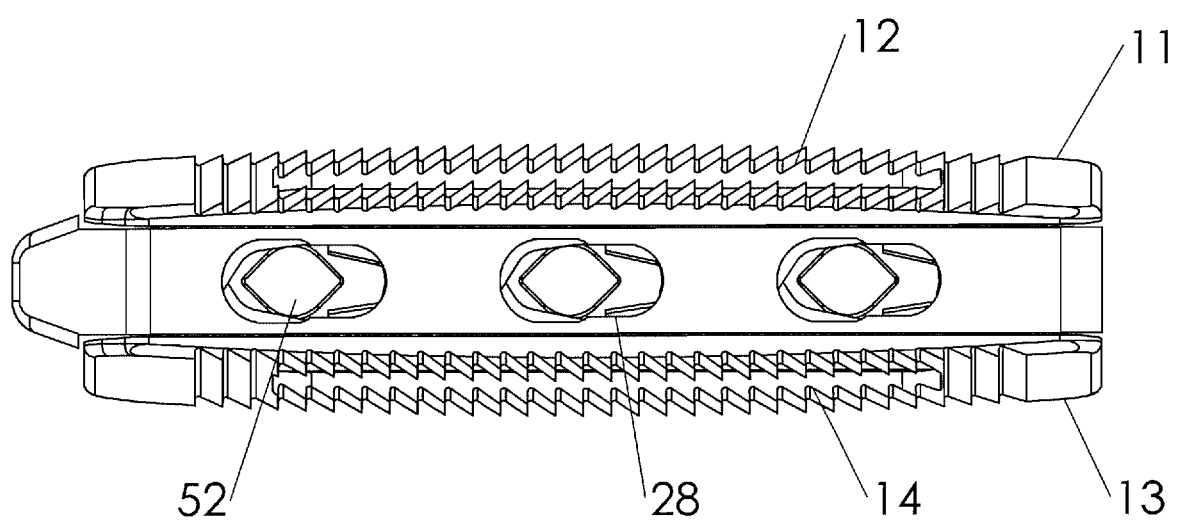
FIG. 11 is a right side view thereof in an expanded position.
Figure 12:
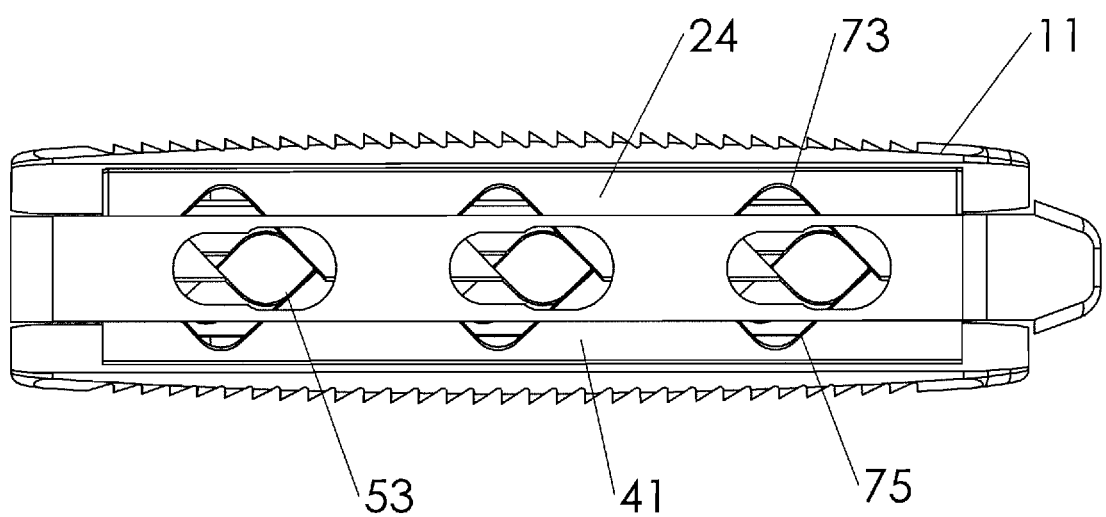
FIG. 12 is a left side view thereof in an expanded position.
Figure 13:
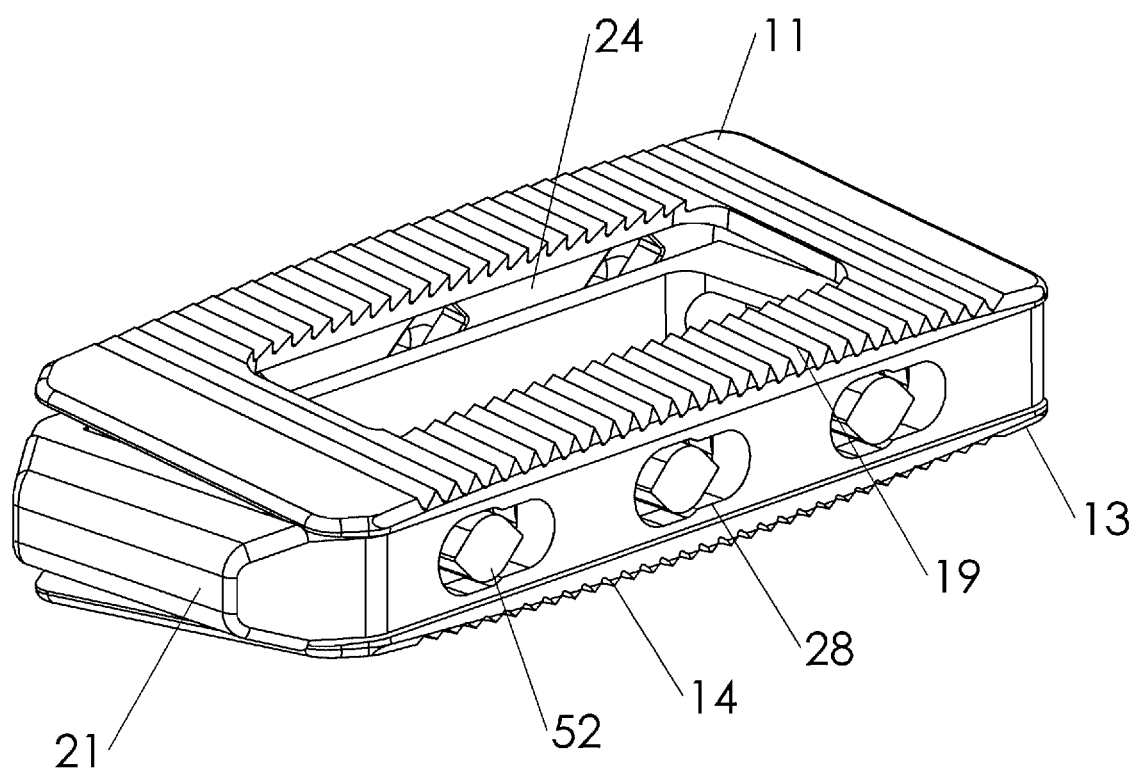
FIG. 13 is a front right perspective view thereof in an expanded position.
Figure 14:
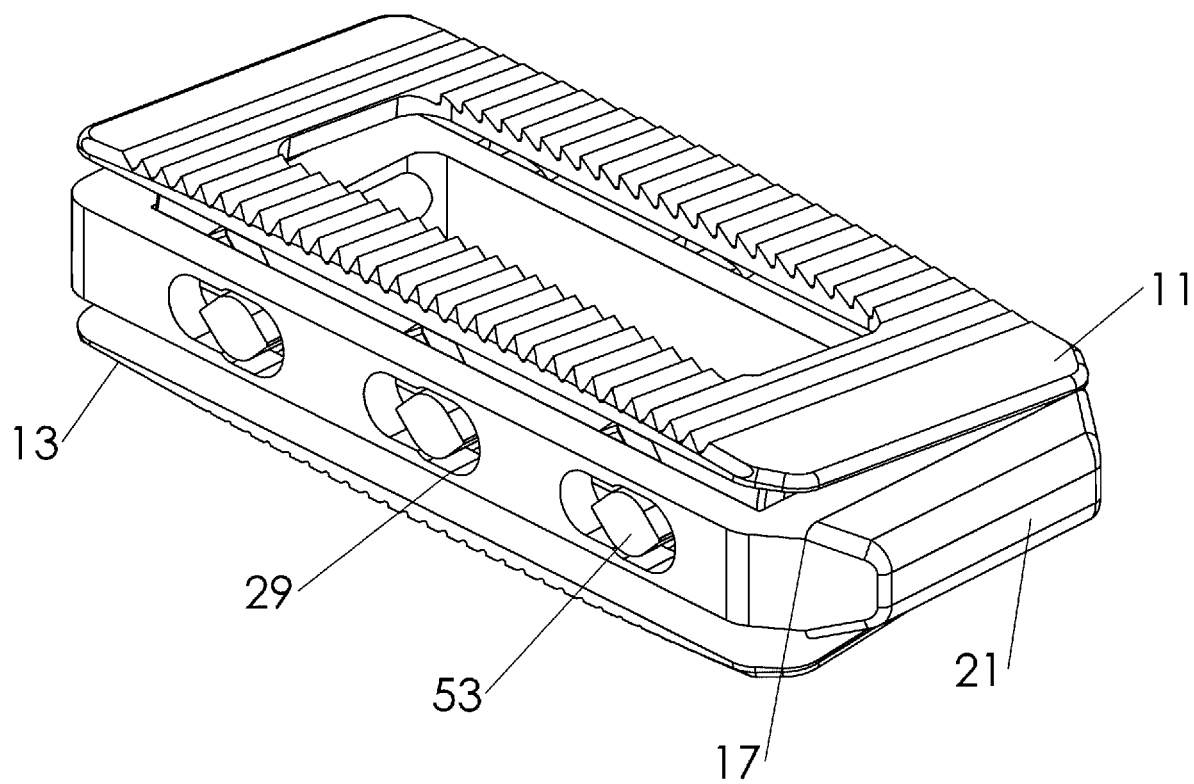
FIG. 14 is a front left perspective view thereof in an expanded position.
Figure 15:
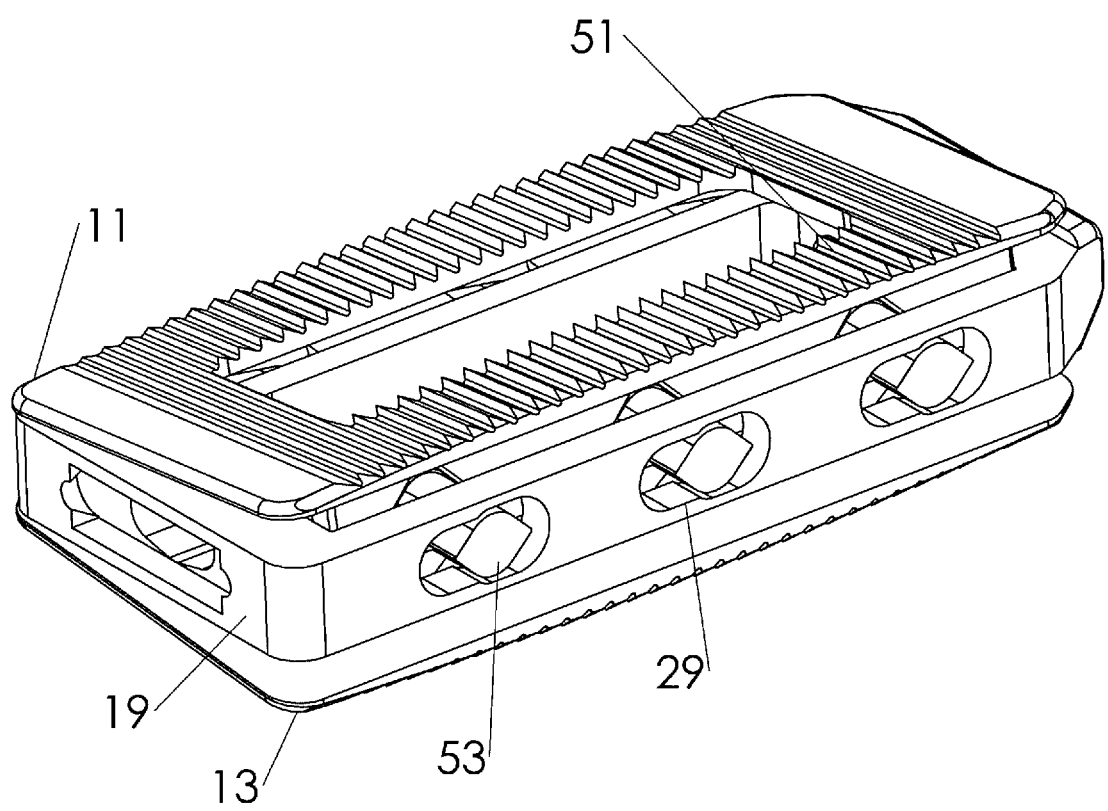
FIG. 15 is a rear right perspective view thereof in an expanded position.

The device 10 has two extreme positions and is adjustable infinitely between these positions. In a non-expanded position, FIGS. 1-7, the upper and lower sections 11, 13 are formed in a parallel position. In an expanded position, FIGS. 9-15, the upper and lower sections 11, 13 are placed in a non-parallel position. In an expanded position, the height of the upper section 11 and the lower section 13 are limited by the straight slope of grooves 73 and 75.

The angle of the slots or grooves are positioned relative to the horizontal planar surface of the upper section 11 and can vary so that the maximum expanded position can be increased or decreased. For example, with the groove close to vertical at a 90° angle to the horizontal plane, the maximum expanded position will be greater than if the slot or groove is at a 45° angle relative to the horizontal plane. However, it is to be understood that a slot or groove having, for example, a 45° angle to the horizontal plane would not only expand the upper section 11 vertically, but also displace the distractor 55 horizontally. The slot or groove engages the protruding members of the distractor 55 to guide the relative movement of the upper section 11, maintaining the distractor 55 and the depending sidewall 23 in alignment.

The openings 20 and 77 facilitate bone in-growth after implantation. The protruding members 52, 53 can be any type, size or shape; for example, rollers, pins, as long as these protruding members 52, 53 can be engaged by the slots or grooves 70, 71, 73, 75. The angle of the slots or grooves 75 of the bottom depending side wall 41 relative to the angle of the slots or grooves 73 of the upper depending sidewall 24 is greater than 0° and up to 180°. The slots or grooves 70, 71 engage the protruding members, rollers or pins 52 of the distractor 55 to guide the relative movement of the upper and lower sections 11, 13, maintaining the distractor 55 and the depending sidewalls in alignment.

The depending sidewalls of the upper and lower sections, and the slots or grooves of each sidewall are smooth to provide ease in the relative sliding contact between the sidewalls and between the protruding members 52, 53 of the distractor 55. In alternative embodiments, the slots or grooves may comprise jagged steps, which are positioned to provide a lock-step expansion when the device is expanded.

The invention has been described in detail with reference to preferred embodiments thereof. However, it will be appreciated that those skilled in the art, upon consideration of this disclosure, may make modifications and improvements within the spirit and scope of the invention. The following non-limiting examples are illustrative of the invention.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

What is claimed is:

1. A spinal fusion device for adjusting the space between vertebrae comprising:
    an upper section having a top surface for contacting one vertebra and a first sidewall extending downwardly away from said top surface having a plurality of angle sloped grooves and a second sidewall extending away from said top surface having a plurality of straight sloped grooves; a lower section having a bottom surface for contacting one vertebra and a first sidewall extending upwardly away from said bottom surface having a plurality of angle sloped grooves and a second sidewall extending upwardly away from said bottom surface having a plurality of straight sloped grooves, said angle sloped grooves of said upper and lower section are dissimilar to said straight sloped grooves of said upper and lower section, said first and second sidewalls of said upper section nesting with said first and second sidewalls of said lower section;
    a distractor positionable between said lower section sidewalls having a first set of protruding members positioned on one side of said distractor constructed and arranged to extend through said angle sloped grooves of said upper and lower section, and a second set of protruding members positioned on an opposite side of said distractor constructed and arranged to extend through said straight sloped grooves of said upper and lower sections;
    a body member having a first and second sidewall positioned outboard of said upper section sidewall, and a front end and a rear end, said first sidewall having apertures for receiving a portion of said first set of protruding members, and second sidewall having apertures for receiving a portion of said second set of protruding members; and
    an actuator for adjusting said distractor in relation to said body member, wherein movement of said actuator causes said upper and lower sections to tilt.

2. The spinal fusion device of claim 1, wherein the distance between the top and bottom surfaces increases unevenly to form a substantially wedge shape, angled towards a sidewall.

3. The spinal fusion device of claim 1, wherein said distractor and said body member includes an opening for accessing an actuator position along an inner surface of said distractor.

4. The spinal fusion device of claim 1, wherein the upper and lower surfaces include friction teeth.

5. The spinal fusion device of claim 1, wherein the body member is dimensioned to fit bone or bone graft material.

6. The spinal fusion device of claim 1, wherein the distractor is slidably movable within said body member.

7. The spinal fusion device of claim 1, wherein an opening on a first end of the body member comprises threads for engaging said actuator and is aligned with an opening in the distractor for receiving said actuator and to move the distractor relative to the depending sidewalls as said actuator is threaded into said opening in said first end of said body member.

8. The spinal fusion device of claim 1, wherein the first and second sidewalls of the upper section, having a groove for engaging the protruding members of the distractor, are dimensioned to slidably fit into the lower section having a groove, whereby the distance between the bottom surface and the top surface is adjustable by moving said distractor relative to said body member.

9. The spinal fusion device of claim 8, wherein the protruding members of the distractor slidably move in grooves in a first direction when the distractor is actuated and the distance between the upper and lower section decreases on a side, or the protruding members of the distractor move in the grooves in a second direction opposite to the first direction when the distractor is actuated and the distance between the upper and lower section increases on the side.

* * * * *